United States Patent [19]

Oda et al.

[11] 3,965,163

[45] June 22, 1976

[54] PROCESS FOR PREPARING UNSATURATED CARBOXYLIC ACIDS FROM THE CORRESPONDING UNSATURATED ALDEHYDES

[75] Inventors: Yoshio Oda; Keiichi Uchida; Takeshi Morimoto, all of Yokohama, Japan

[73] Assignee: Asahi Glass Co., Ltd., Tokyo, Japan

[22] Filed: Mar. 15, 1974

[21] Appl. No.: 451,443

[30] Foreign Application Priority Data

Mar. 16, 1973  Japan............................. 48-29943
Mar. 16, 1973  Japan............................. 48-29944

[52] U.S. Cl............................ 260/530 N; 252/435; 252/437; 260/530 R
[51] Int. Cl.$^2$........................................ C07C 51/26
[58] Field of Search............................. 260/530 N

[56] References Cited

UNITED STATES PATENTS

| | | | |
|---|---|---|---|
| 3,087,964 | 4/1963 | Koch et al. | 260/530 N |
| 3,574,729 | 4/1971 | Gasson | 260/530 N |
| 3,773,692 | 11/1973 | Hensel et al. | 260/530 N |

*Primary Examiner*—Vivian Garner
*Attorney, Agent, or Firm*—Oblon, Fisher, Spivak, McClelland & Maier

[57] ABSTRACT

Unsaturated carboxylic acids are prepared by reacting the corresponding unsaturated aldehyde with molecular oxygen in the presence of a catalyst of (a) molybdenum, (b) phosphorus, (c) antimony, (d) at least one element selected from the group consisting of tungsten, barium, chromium, lead, niobium, tantalum, tin, nickel, iron and zirconium, and (e) oxygen, and optionally (f) at least one element selected from the group consisting of strontium, titanium, germanium, cerium, and silver.

8 Claims, No Drawings

PROCESS FOR PREPARING UNSATURATED CARBOXYLIC ACIDS FROM THE CORRESPONDING UNSATURATED ALDEHYDES

BACKGROUND OF THE INVENTION

1. Field of the Invention

This invention relates to a process for preparing unsaturated carboxylic acids having from three to four carbon atoms by the catalytic vapor phase oxidation of the corresponding unsaturated aldehyde. More particularly, this invention relates to a process for preparing methacrylic acid from methacrolein, characterized mainly by the use of novel catalysts.

2. Description of the Prior Art

Many catalysts useful for the preparation of unsaturated carboxylic acids having from three to four carbon atoms by the catalytic vapor phase oxidation of the corresponding unsaturated aldehydes with molecular oxygen have already been proposed. Some of those are excellent for preparing acrylic acid from acrolein and have been used for the production of acrylic acid on a large scale. Various catalysts for preparing methacrylic acid from methacrolein have also been proposed. However, methacrylic acid has not been produced commercially from methacrolein by use of these catalysts because of the low yield. This is because methacrolein is more combustible than acrolein, i.e., it is subjected to complete oxidation to carbon monoxide and/or carbon dioxide rather than to partial oxidation to the desired product, and because methacrolein is easily polymerizable to heavy compounds. There currently exists no completely satisfactory catalyst for the preparation of methacrylic acid. U.S. Pat. Nos. 3,358,020 and 3,453,069 disclose prior art catalysts which slow excellent results for the production of acrylic acid (the conversion of acrolein is 96–100%, while the selectivity to acrylic acid is 80–90%), but not for the production of methacrylic acid (the conversion of methacrolein is 29–63%, while the selectivity to methacrylic acid is 11–41%).

A need exists, therefore, for a catalyst which minimizes or eliminates the oxidative side reactions and the polymerization reactions which occur in the conversion of acrolein and methacrolein to their respective acid derivatives.

SUMMARY OF THE INVENTION

Accordingly, it is one object of this invention to provide a method for preparing methacrylic acid from its aldehyde precursors in yields which are superior to those attained from prior art processes.

Another object of this invention is to provide a novel catalyst for the preparation of unsaturated carboxylic acids from the corresponding unsaturated aldehydes and a method for the preparation thereof.

Briefly, these and other objects of the present invention, as will hereinafter become more readily understood can be attained by a process for preparing unsaturated carboxylic acids by the oxidation of the corresponding unsaturated aldehydes with molecular oxygen in the vapor phase at a temperature of from 250°C to 450°C., in the presence of a catalyst consisting essentially of (a) molybdenum, (b) phosphorus, (c) antimony, (d) at least one element selected from the group consisting of tungsten, barium, chromium, lead, niobium, tantalum, tin, nickel, iron, and zirconium, and (e) oxygen, and optionally (f) at least one element selected from the group consisting of strontium, titanium, germanium, cerium and silver.

DETAILED DESCRIPTION OF PREFERRED EMBODIMENTS

According to the process of this invention, typical values obtained for the conversion and selectivity of methacrolein to methacrylic acid range from 60–90 and 70–85, respectively. For the oxidation of acrolein to acrylic acid, the conversion and selectivity values range from 96–100 and 80–85, respectively.

The catalysts have the desired catalytic activity only when they contain all of the essential components. If the catalyst lacks one or more of the essential components, the catalytic activity is very low, which results in small amounts of the desired unsaturated carboxylic acids. Thus, these catalysts are unsatisfactory for commercial applications. Catalysts of this invention which contain all of the essential components have very good catalytic activity. The preferred catalysts of the invention are characterized by an empirical formula which in part contains 12 molybdenum atoms as follows:

$$Mo_{12} - P_\alpha - Sb_\beta - X_\gamma - O_\delta \qquad 1.$$

wherein X is at least one element selected from the group consisting of W, Ba, Cr, Pb, Nb, Ta, Sn, Ni, Fe and Zr; $\alpha$ is a number from 0.1 to 3, preferably 1 to 2; $\beta$ is a number from 0.1 to 9, preferably 0.5 to 5; $\gamma$ is a number from 0.1 to 7, preferably 1 to 5; $\delta$ is decided on the basis of the oxidation states of Mo and P and Sb and X elements, and $\delta$ is 36 to 87 when each component is in a highly oxidized state. The catalysts having the above empirical formula wherein X is W, Ba, Fe, Zr or Cr or combination thereof, exhibit superior characteristics.

In addition to the essential components above, the catalysts of this invention may contain at least one element selected from the group consisting of Sr, Ti, Ge, Ce, and Ag, thereby improving their catalytic activity. These elements are not essential, but are optional components. When the catalyst of this invention contains the optional components above, their preferred empirical formula may be expressed as follows:

$$Mo_{12} - P_\alpha - Sb_\beta - X_\gamma - Y_\epsilon - O_\delta \qquad 2.$$

wherein X is at least one element selected from the group consisting of W, Ba, Cr, Pb, Nb, Ta, Sn, Ni, Fe and Zr; Y is at least one element selected from the group consisting of Sr, Ti, Ge, Ce, and Ag; $\alpha$, $\beta$, $\gamma$ are the same as in formula (1); $\epsilon$ is a number from 0.1 to 7, preferably 0.5 to 5; $\delta$ is decided on the basis of the oxidation states of Mo, P, Sb, X and Y, and when each component is in a highly oxidized state, $\delta$ is a number between 44 and 108.

In particular when the catalysts contain the optional element, preferred catalysts of this invention may be expressed by the following three formulas:

$$Mo_{12} - P_\alpha - Sb_\beta - X_\gamma - Y_\epsilon - O_\delta \qquad 3.$$

wherein X is at least one element selected from the group consisting of W, Ba, Cr and Pb; Y is at least one element selected from the group consisting of Sr, Nb, Ta, Ce, Fe, Zr and Ni: $\alpha$, $\beta$, $\gamma$, $\delta$ and $\epsilon$ are the same as in formula (2).

$$Mo_{12} - P_\alpha - Sb_\beta - X_\gamma - Y_\epsilon - O_\delta \qquad 4.$$

wherein X is at least one element selected from the group consisting of Nb, Ta, Sn and Ni; Y is at least one element selected from the group consisting of Zr, Sr, and Ti; $\alpha$, $\beta$, $\gamma$, $\delta$ and $\epsilon$ are the same as in formula (2)

$$Mo_{12} - P_\alpha - Sb_\beta - X_\gamma - Y_\epsilon - O_\delta \qquad 5.$$

wherein X is at least one element selected from the group consisting of Fe, Zr; Y is at least one element selected from the group consisting of Ge, Ce, Ag and Ti; $\alpha$, $\beta$, $\gamma$, $\delta$ and $\epsilon$ are the same as in formula (2).

If the foregoing catalyst of this invention contains any further elements the catalytic activity is adversely affected.

The catalyst of this invention may be prepared by any one of several methods. Preferably, the catalyst may be prepared by concentrating a solution or a suspension containing the desired components and drying the resulting concentrate. Thereafter, the dried product is preferably calcined in air at a temperature of from 150° to 500°C., preferably 200° to 420°C, for about 1 to about 48 hours. The calcined product is then ground to 35 to 100 mesh, which is suitable for use. The prepared catalyst has a specific surface area of 0.1 to 50m²/g.

The exact chemical structure of the catalysts of this invention is not completely known. However, it can reasonably be presumed that the catalyst is a homogeneous mixture of the oxides of all the components, or a compound or a complex formed by the reaction of phosphomolybdate and the oxides of the other components. In particular it is found that the catalysts containing antimony molybdenate impart superior characteristics to the material.

In some cases, in order to improve the physical properties of the catalysts, they are preferably supported on a suitable carrier, such as silica, silica-containing materials, silicon carbide, alumina and the like. The amount of the carrier used is preferably in the range of 30 to 97% by weight based on the supported catalyst.

The starting materials of each component used in the preparation of the catalysts are listed as follows: Suitable sources of molybdenum include, ortho, meta- or paramolybdic acid, ortho, meta- or paramolybdates, heteropolymolybdic acid, heteropolymolybdates, molybdenum oxide and the like. Suitable sources of phosphorus include phosphoric acid, phosphates, polyphosphoric acid, polyphosphates and the like. Phosphomolybdic acid or phosphomolybdates may effectively be used as a common staring material for both the molybdenum and the phosphorus compounds. Suitable sources of antimony include antimony chloride, antimony oxide, antimony sulphate etc. Suitable sources of tungsten include tungsten trioxide, tungsten acid, salts of tungsten acids and the like. Suitable sources of barium are barium oxide, barium nitrate, etc. Suitable sources of chromium include chromium oxide, chromium nitrate, chromium sulfate, and the like. Suitable sources of lead include lead oxide, lead nitrate etc. Suitable sources of niobium include niobium oxide, niobium hydroxide, niobium nitrate, and the like. A suitable source of tantalum is tantalum pentaoxide. Suitable sources of tin include tin oxide, tin chloride etc. Suitable sources of nickel include nickel nitrate, nickel chloride, and the like. Suitable sources of iron include iron oxide, iron nitrate, iron chloride, etc. Suitable sources of zirconium include zirconium oxide, zirconium nitrate etc. Suitable sources of strontium include strontium oxide, strontium nitrate and the like. Suitable sources of titanium include titanium tetrachloride, titanium oxide etc. Suitable sources of germanium include germanium oxide, germanium tetrachloride, and the like. Suitable sources of cerium include cerium oxide, cerium nitrate etc. Suitable sources of silver include silver oxide, silver nitrate and the like.

The essential reactants of this invention are the unsaturated aldehydes, namely acrolein and methacrolein, and molecular oxygen which may be administered as pure oxygen, oxygen diluted with inert gases, oxygen enriched air or air without additional oxygen. Air is economically the most practical source of molecular oxygen. The reaction of this invention may be conducted in either a fixed or fluidized catalyst bed. The reaction temperature may vary from 230° to 450°C., preferably from 250° to 380°C. The reaction pressure may vary from 0.5 to 40 atmospheres absolute, prefereably from about 1 to 10 atmospheres absolute. When the reaction pressure is relatively high within the indicated range, the reaction temperature may be somewhat lower within the indicated range. Contact time usually varies from 0.2 to 30 seconds, preferably from 1 to 20 seconds. The molecular ratio of oxygen to unsaturated aldehydes in the feed gas usually varies from 1 : 10 to 10 : 1, preferably from 1 : 3 to 3 : 1.

Steam may be added to the gaseous reaction mixture, which improves the yield of unsaturated carboxylic acids. In addition, nitrogen, saturated hydrocarbons such as methane, propane, butane or the like, or other inert gases may also be added to the gaseous reactant mixture. The concentration of the steam may vary from 2 to 80%, preferably from 10 to 50% of the volume of the feed.

Since the reaction of this invention is exothermic, the temperature within the reactor must be regulated in order to control the reaction. Thus the reactor is preferably placed in a fluidized solid bath, a molten salt bath or a metal bath. The methacrylic acid or acrylic acid may be recovered from the reaction product by any one of the conventional methods. Suitable separation techniques include condensation and/or extraction followed by distillation.

The following definitions apply to the conversion of unsaturated aldehydes, and to the selectivity and yield of unsaturated carboxylic acids. All the analyses were conducted by means of gas chromatography.

$$\text{Conversion Percent} = \frac{\text{Unsaturated aldehyde in the feed (moles)} - \text{Unsaturated aldehyde in the effluent (moles)}}{\text{Unsaturated aldehyde in the feed (moles)}} \times 100$$

$$\text{Selectivity (percent) (Unsaturated carboxylic acid)} = \frac{\text{Unsaturated carboxylic acid in the effluent (mole)}}{\text{Unsaturated aldehyde in the feed (moles)} - \text{Unsaturated aldehyde in the effluent (moles)}} \times 100$$

$$\text{Selectivity (acetic acid) (percent)} = \frac{\text{Acetic acid in the effluent (mole)}}{\text{Unsaturated aldehyde in the feed (moles)} - \text{Unsaturated aldehyde in the effluent (moles)}} \times 100 \times \tfrac{1}{2}$$

Having generally described the invention, a further understanding can be obtained by reference to the following Examples which are provided for purposes of illustration only and are not to be construed as limiting of the invention unless otherwise specified.

stead of tungsten trioxide, so as to give the atomic ratio values shown in Table 1.

The catalysts were used for the oxidation of methacrolein under substantially the same conditions as those of Example 1. The results obtained are shown in Table 1.

TABLE 1

| Example No. | Catalysts | Methacrolein conversion (%) | Methacrylic acid selectivity (%) | Acetic acid selectivity (%) |
|---|---|---|---|---|
| 2 | $Sb_1Mo_{12}Ba_1P_1O_{39.5}$ | 89 | 69 | 12 |
| 3 | $Sb_1Mo_{12}Pb_1P_1O_{39.5}$ | 85 | 53 | 11 |
| 4 | $Sb_1Mo_{12}Cr_1P_1O_{40}$ | 90 | 74 | 11 |
| 5 | $Sb_1Mo_{12}W_1Ba_1P_1O_{41.5}$ | 70 | 88 | 7 |
| 6 | $Sb_1Mo_{12}W_1Cr_1P_1O_{43}$ | 90 | 70 | 12 |
| 7 | $Sb_1Mo_{12}W_1Pb_1P_1O_{42.5}$ | 78 | 67 | 9 |
| 8 | $Sb_1Mo_{12}Ba_1Pb_1P_1O_{40.5}$ | 75 | 65 | 14 |
| 9 | $Sb_1Mo_{12}Ba_1Cr_1P_1O_{41}$ | 74 | 69 | 8 |
| 10 | $Sb_1Mo_{12}Cr_1Pb_1P_1O_{41}$ | 85 | 55 | 7 |

EXAMPLE 1

A solution of 5.7 g of antimony trichloride dissolved in 100 cc of 6N-HCl was added with stirring to a solution of 58 g of phosphmolybdic acid ($P_2O_5 \cdot 24MoO_3 \cdot 48H_2O$) dissolved in 150 cc of water. To the resulting solution was added 5.8 g of tungsten trioxide powder. The mixture was heated with stirring to concentrate it. The resultant cake was dried at 120°C for 12 hours and the dried product was calcined at 380°C for 12 hours to yield a solid having the following empirical formula $Sb_1Mo_{12}W_1P_1O_{41.5}$ The solid was passed through a sieve to yield catalyst particles of 35–100 mesh. An empty U-shaped ractor having an inner diameter of 8mm was filled with 4 ml. of the catalyst. The reactor was placed into a molten salt bath heated to 320°C. A gaseous reaction mixture composed of 55% nitrogen, 30% steam, 10% oxygen, and 5% methacrolein (percent by volume) was passed through the reactor with a contact time of 2 seconds. The following results were obtained.

| | |
|---|---|
| Conversion of methacrolein | 89% |
| Selectivity to methacrylic acid | 72% |
| Selectivity to acetic acid | 11.0% |

EXAMPLES 2–10

Catalysts were prepared in a manner similar to that of Example 1, except that 3.8 g of barium oxide, 5.6 g of lead oxide or 1.9 g of chromium oxide were used in-

REFERENCE A

Catalysts were prepared in a manner similar to that of Examples 1–10 so as to give the atomic ratio values shown in Table 2. The reaction of Example 1 was repeated by using the catalysts. The results obtained are shown in Table 2.

TABLE 2

| Reference No. | Catalysts | Methacrolein conversion (%) | Methacrylic acid selectivity (%) | Acetic acid selectivity (%) |
|---|---|---|---|---|
| 1 | $Sb_1Mo_{12}P_1O_{38.5}$ | 90 | 23 | 26 |
| 2 | $Sb_1Mo_{12}W_1O_{40.5}$ | 40 | 20 | 11 |
| 3 | $Sb_1Mo_{12}Ba_1O_{38.5}$ | 33 | 17 | 6 |
| 4 | $Sb_1Mo_{12}Sn_1O_{39.5}$ | 35 | 26 | 7 |
| 5 | $Mo_{12}Zr_1P_1O_{40.5}$ | 28 | 24 | 14 |
| 6 | $Mo_{12}P_1O_{38.5}$ | 64 | 31 | 5 |

EXAMPLE 11

A solution of 5.7 g of antimony trichloride dissolved in 100 cc of 6N-HCl was added with stirring to a solution of 58 g of phosphomolybdic acid ($P_2O_5 \cdot 24MoO_3 \cdot 48H_2O$) dissolved in 150 cc of water. To the resulting solution was added 5.8 g of tungsten trioxide powder followed by the addition of 3.3 g of niobium pentaoxide. The mixture was heated with stirring to concentrate it. The resultant cake was dried at 120°C for 12 hours and the dried product was calcined at 400°C for 12 hours to yield a solid having the following empirical formula $Sb_1Mo_{12}W_1Nb_1P_1O_{44}$ The solid was passed through a sieve to yield catalyst particles of 35–100 mesh. An empty U-shaped reactor having inner diameter of 8 mm was filled with 4 ml. of the catalyst.

The catalyst was used for the oxidation of methacrolein under substantially the same conditions as those employed in Example 1. The following results were obtained.

| Conversion of methacrolein | 87% |
| Selectivity to methacrylic acid | 65% |
| Selectivity to acetic acid | 12% |

EXAMPLES 12–35

Catalysts were prepared in a manner similar to that of Example 11, except that 3.8 g of barium oxide, 5.6 g of lead oxide or 1.9 g of chromium oxide were used instead of tungsten oxide, and 2.6 g of strontium oxide, 4.3 g of cerium oxide, 4.1 g of iron oxide, 3.1 g of zirconium oxide or 1.9 g of nickel oxide were used instead of niobium oxide, so as to give the emperical formula shown in Table 3. The reaction of Example 1 was repeated using the catalysts. The following results were obtained.

TABLE 3

| Example No. | Catalysts | Methacrolein conversion (%) | Methacrylic acid selectivity (%) | Acetic acid selectivity (%) |
|---|---|---|---|---|
| 12 | $Sb_1Mo_{12}W_1Sr_1P_1O_{42.5}$ | 89 | 64 | 9 |
| 13 | $Sb_1Mo_{12}W_1Ce_1P_1O_{43.5}$ | 88 | 50 | 12 |
| 14 | $Sb_1Mo_{12}W_1Fe_1P_1O_{44}$ | 82 | 59 | 11 |
| 15 | $Sb_1Mo_{12}W_1Zr_1P_1O_{43.5}$ | 87 | 55 | 10 |
| 16 | $Sb_1Mo_{12}W_1Ni_1P_1O_{42.5}$ | 83 | 57 | 8 |
| 17 | $Sb_1Mo_{12}Ba_1Ta_1P_1O_{42}$ | 83 | 62 | 9 |
| 18 | $Sb_1Mo_{12}Ba_1Sr_1P_1O_{40.5}$ | 80 | 60 | 12 |
| 19 | $Sb_1Mo_{12}Ba_1Ce_1P_1O_{41.5}$ | 85 | 63 | 8 |
| 20 | $Sb_1Mo_{12}Ba_1Fe_1P_1O_{41.5}$ | 82 | 61 | 9 |
| 21 | $Sb_1Mo_{12}Ba_1Zr_1P_1O_{41.5}$ | 75 | 67 | 7 |
| 22 | $Sb_1Mo_{12}Ba_1Ni_1P_1O_{40.5}$ | 72 | 62 | 6 |
| 23 | $Sb_1Mo_{12}Pb_1Nb_1P_1O_{42}$ | 94 | 59 | 14 |
| 24 | $Sb_1Mo_{12}Pb_1Sr_1P_1O_{40.5}$ | 75 | 57 | 17 |
| 25 | $Sb_1Mo_{12}Pb_1Ce_1P_1O_{41.5}$ | 73 | 55 | 14 |
| 26 | $Sb_1Mo_{12}Pb_1Fe_1P_1O_{42}$ | 85 | 54 | 12 |
| 27 | $Sb_1Mo_{12}Pb_1Zr_1P_1O_{41.5}$ | 83 | 57 | 11 |
| 28 | $Sb_1Mo_{12}Pb_1Ni_1P_1O_{40.5}$ | 87 | 51 | 11 |
| 29 | $Sb_1Mo_{12}Cr_1Ta_1P_1O_{42.5}$ | 91 | 57 | 11 |
| 30 | $Sb_1Mo_{12}Cr_1Sr_1P_1O_{41}$ | 83 | 70 | 13 |
| 31 | $Sb_1Mo_{12}Cr_1Ce_1P_1O_{42}$ | 85 | 55 | 9 |
| 32 | $Sb_1Mo_{12}Cr_1Fe_1P_1O_{41.5}$ | 90 | 51 | 7 |
| 33 | $Sb_1Mo_{12}Cr_1Zr_1P_1O_{42}$ | 86 | 52 | 10 |
| 34 | $Sb_1Mo_{12}Cr_1Ni_1P_1O_{41}$ | 88 | 64 | 10 |

EXAMPLES 35–68

The catalysts prepared by the procedure of Examples 1–34 were used for the oxidation of acrolein instead of methacrolein under substantially the same conditions as those employed in Example 1, except that the reaction temperature was 360°C. The results are shown in Table 4.

TABLE 4

| Example No. | Catalysts | Acrolein conversion (%) | Acrylic acid selectivity (%) | Acetic acid selectivity (%) |
|---|---|---|---|---|
| 35 | $Sb_1Mo_{12}W_1P_1O_{41.5}$ | 85 | 80 | 5 |
| 36 | $Sb_1Mo_{12}Ba_1P_1O_{39.5}$ | 91 | 77 | 4 |
| 37 | $Sb_1Mo_{12}Pb_1P_1O_{39.5}$ | 95 | 72 | 3 |
| 38 | $Sb_1Mo_{12}Cr_1P_1O_{40}$ | 75 | 78 | 5 |
| 39 | $Sb_1Mo_{12}W_1Ba_1P_1O_{42.5}$ | 94 | 81 | 9 |
| 40 | $Sb_1Mo_{12}W_1Cr_1P_1O_{43}$ | 96 | 77 | 16 |
| 41 | $Sb_1Mo_{12}W_1Pb_1P_1O_{42.5}$ | 92 | 73 | 13 |
| 42 | $Sb_1Mo_{12}Ba_1Cr_1P_1O_{41}$ | 95 | 72 | 14 |
| 43 | $Sb_1Mo_{12}W_1Nb_1P_1O_{44}$ | 97 | 82 | 4 |
| 44 | $Sb_1Mo_{12}W_1Ce_1P_1O_{43.5}$ | 85 | 75 | 8 |
| 45 | $Sb_1Mo_{12}W_1Zr_1 P_1O_{43.5}$ | 96 | 80 | 9 |
| 46 | $Sb_1Mo_{12}W_1Ni_1P_1O_{42.5}$ | 89 | 71 | 11 |
| 47 | $Sb_1Mo_{12}Ba_1Sr_1P_1O_{40.5}$ | 86 | 69 | 12 |
| 48 | $Sb_1Mo_{12}Ba_1Ce_1P_1O_{41.5}$ | 97 | 66 | 14 |
| 49 | $Sb_1Mo_{12}Ba_1Zr_1P_1O_{41.5}$ | 95 | 68 | 13 |
| 50 | $Sb_1Mo_{12}Ba_1Ni_1P_1O_{40.5}$ | 88 | 66 | 11 |
| 51 | $Sb_1Mo_{12}Pb_1Sr_1P_1O_{40.5}$ | 90 | 69 | 10 |
| 52 | $Sb_1Mo_{12}Pb_1Ce_1P_1O_{41.5}$ | 91 | 66 | 11 |
| 53 | $Sb_1Mo_{12}Pb_1Fe_1P_1O_{42}$ | 89 | 71 | 9 |
| 54 | $Sb_1Mo_{12}Pb_1Zr_1P_1O_{41.5}$ | 91 | 65 | 11 |
| 55 | $Sb_1Mo_{12}Pb_1Ni_1P_1O_{40.5}$ | 95 | 61 | 10 |
| 56 | $Sb_1Mo_{12}Cr_1Nb_1P_1O_{42.5}$ | 93 | 77 | 5 |
| 57 | $Sb_1Mo_{12}Cr_1Ce_1P_1O_{42}$ | 90 | 70 | 10 |
| 58 | $Sb_1Mo_{12}Cr_1Fe_1P_1O_{41.5}$ | 95 | 72 | 6 |
| 59 | $Sb_1Mo_{12}Cr_1Ni_1P_1O_{41}$ | 92 | 60 | 7 |

EXAMPLES 60–73

Catalysts were prepared in a manner similar to that of Example 1 so as to give the atomic ratio values shown in Table 5. The reaction of Example 1 was repeated using the catalysts. The results obtained are shown in Table 5.

TABLE 5

| Example No. | Catalysts | Methacrolein conversion (%) | Methacrylic selectivity (%) | Acetic acid selectivity (%) |
|---|---|---|---|---|
| 60 | $Sb_3Mo_{12}W_1P_1O_{41.5}$ | 90 | 75 | 12 |
| 61 | $Sb_1Mo_{12}W_3P_1O_{47.5}$ | 93 | 63 | 14 |
| 62 | $Sb_1Mo_{12}W_1P_3O_{46.5}$ | 50 | 54 | 5 |
| 63 | $Sb_1Mo_{12}W_3P_1O_{47.5}$ | 85 | 71 | 10 |
| 64 | $Sb_6Mo_{12}W_1P_1O_{41.5}$ | 89 | 69 | 11 |
| 65 | $Sb_1Mo_{12}W_6P_1O_{56.5}$ | 82 | 65 | 7 |
| 66 | $Sb_9Mo_{12}W_1P_1O_{41.5}$ | 75 | 59 | 5 |
| 67 | $Sb_9Mo_{12}W_9P_1O_{65.5}$ | 72 | 53 | 6 |
| 68 | $Sb_1Mo_{12}W_3Ba_1P_1O_{48.5}$ | 91 | 71 | 13 |
| 69 | $Sb_3Mo_{12}W_1Ba_1P_1O_{42.5}$ | 86 | 75 | 10 |
| 70 | $Sb_3Mo_{12}W_1Ba_3P_1O_{44.5}$ | 84 | 73 | 9 |
| 71 | $Sb_1Mo_{12}W_1Ba_6P_1O_{40.5}$ | 77 | 65 | 7 |
| 72 | $Sb_1Mo_{12}W_6Ba_3P_1O_{59.5}$ | 70 | 60 | 4 |
| 73 | $Sb_6Mo_{12}W_1Ba_1P_1O_{42.5}$ | 87 | 68 | 11 |

EXAMPLE 74

A solution of 5.7 g of antimony trichloride dissolved in 100 cc of 6N-HCl was added with stirring to a solution of 58 g of phosphomolybdic acid $)P_2O_5 \cdot 2 \cdot 4MoO_3 \cdot 48H_2O)$ dissolved in 150 cc of water. To the resulting solution was added 2.0 g of iron oxide ($Fe_2O_3$) powder.

The mixture was heated with stirring to concentrate it. The resultant cake was dried at 120°C for 12 hours and the dried product was calcined at 380°C for 12 hours to yield a solid having the following empirical formula $$Sb_1Mo_{12}Fe_1P_1O_{40}$$

The solid was passed through a sieve to yield catalyst particles of 35–100 mesh.

An empty U-shaped reactor having inner diameter of 8 mm was filled with 4 ml of the catalyst. The reactor was placed into a molten salt bath heated at 320°C. A gaseous reactant mixture composed of 55% nitrogen, 30% steam, 10% oxygen and 5% methacrolein (percent by volume) was passed through the reactor with a contact time of 4 seconds. The following results were obtained.

| | |
|---|---|
| Conversion of methacrolein | 93% |
| Selectivity to methacrylic acid | 55% |
| Selectivity to acetic acid | 10% |

EXAMPLE 75

Catalysts were prepared in a manner similar to that of Example 74, except that zirconium oxide was used instead of iron oxide, so as to give the empirical formula $$Sb_1Mo_{12}Zr_1P_1O_{40.5}$$

The reaction of Example 83 was repeated using the catalyst. The following results were obtained.

| | |
|---|---|
| Conversion of methacrolein | 79% |
| Selectivity to methacrylic acid | 62% |
| Selectivity to acetic acid | 12% |

REFERENCE B

Catalysts were prepared in a manner similar to that of Example 74 so as to give the atomic ratios shown in Table 6. The reaction of Example 83 was repeated using the catalysts. The results obtained are shown in Table 6.

TABLE 6

| Reference No. | Catalysts | Methacrolein conversion (%) | Methacrylic selectivity (%) | Acetic acid selectivity (%) |
|---|---|---|---|---|
| 7 | $Sb_1Mo_{12}P_1O_{38.5}$ | 90 | 25 | 15 |
| 8 | $Sb_1Mo_{12}Zr_1O_{39.5}$ | 40 | 20 | 5 |
| 9 | $Sb_1Mo_{12}Fe_1O_{39}$ | 46 | 23 | 4 |
| 10 | $Mo_{12}Zr_1P_1O_{40.5}$ | 60 | 31 | 7 |
| 11 | $Mo_{12}Zr_1P_1O_{40.5}$ | 70 | 40 | 9 |

EXAMPLE 76

A solution of 5.7 g of antimony trichloride dissolved in 100 cc of 6N-HCl was added with stirring to a solution of 58 g of phosphomolybdic acid ($P_2O_5 \cdot 2 \cdot 4MoO_3 \cdot 48H_2O$) dissolved in 150 cc of water. Powdered iron oxide and zirconium oxide were added to the resulting solution. The mixture was heated with stirring to concentrate it. The resultant cake was dried at 120°C for 12 hours and the dried product was calcined at 400°C for 12 hours to yield a solid having the following empirical formula $$Sb_1Mo_{12}Fe_1Zr_1P_1O_{42}$$

The solid was passed through a sieve to yield catalyst particles of 35–100 mesh.

An empty U-shaped reactor having inner diameter of 8 mm was filled with 4 ml. of the catalyst. The catalyst was used for the oxidation of methacrolein under substantially the same conditions as those employed in Example 1. The following results were obtained.

| | |
|---|---|
| Conversion of methacrolein | 89% |
| Selectivity to methacrylic acid | 68% |
| Selectivity to acetic acid | 8% |

EXAMPLES 77–84

Catalysts were prepared in a manner similar to that of Example 76, except that germanium oxide, cerium oxide, silver oxide or titanium oxide were used with or without iron oxide and zirconium oxide, so as to give the emperical formula shown in Table 7. The reaction of Example 74 was repeated using the catalysts. The following results were obtained.

TABLE 7

| Example No. | Catalysts | Methacrolein conversion (%) | Methacrylic acid selectivity (%) | Acetic acid selectivity (%) |
|---|---|---|---|---|
| 77 | $Sb_1Mo_{12}Fe_1Ge_1P_1O_{42}$ | 90 | 61 | 7 |
| 78 | $Sb_1Mo_{12}Fe_1Ce_1P_1O_{42}$ | 86 | 70 | 7 |
| 79 | $Sb_1Mo_{12}Fe_1Ag_1P_1O_{41}$ | 82 | 71 | 11 |
| 80 | $Sb_1Mo_{12}Fe_1Ti_1P_1O_{42}$ | 75 | 65 | 12 |
| 81 | $Sb_1Mo_{12}Zr_1Ge_1P_1O_{42.5}$ | 71 | 70 | 8 |
| 82 | $Sb_1Mo_{12}Zr_1Ce_1P_1O_{42.5}$ | 93 | 60 | 15 |
| 83 | $Sb_1Mo_{12}Zr_1Ag_1P_1O_{41.5}$ | 90 | 58 | 4 |
| 84 | $Sb_1Mo_{12}Zr_1Ti_1P_1O_{43.5}$ | 79 | 62 | 13 |

EXAMPLES 85–89

The catalysts prepared by the procedure of Examples 74, 75, 76, 77 and 83 were used for the oxidation of acrolein instead of methacrolein under substantially the same conditions as those employed in Example 74, except that the reaction temperature was 380°C. The results are shown in Table 8.

TABLE 8

| Example No. | Catalysts | Acrolein conversion (%) | Acrylic acid selectivity (%) | Acetic acid selectivity (%) |
|---|---|---|---|---|
| 85 | $Sb_1Mo_{12}Fe_1P_1O_{40}$ | 93 | 75 | 10 |
| 86 | $Sb_1Mo_{12}Zr_1P_1O_{40.5}$ | 89 | 72 | 8 |
| 87 | $Sb_1Mo_{12}Fe_1Zr_1P_1O_{42}$ | 84 | 78 | 7 |
| 88 | $Sb_1Mo_{12}Fe_1Ge_1P_1O_{42}$ | 91 | 72 | 9 |
| 89 | $Sb_1Mo_{12}Zr_1Ag_1P_1O_{41.5}$ | 92 | 68 | 6 |

EXAMPLE 90

A solution of 5.7 g of antimony trichloride dissolved in 100 cc of 6N-HCl was added with stirring to a solution of 58 g of phosphomolybdic acid ($P_2O_5 \cdot 2\text{-}4MoO_3 \cdot 48H_2O$) dissolved in 150 cc of water. To the resulting solution was added 3.3 g of niobium pentaoxide. The mixture was heated with stirring to concentrate it. The resultant cake was dried at 120°C for 12 hours and the dried product was calcined at 400°C for 12 hours to yield a solid having the following empirical formula $$Sb_1Mo_{12}Nb_1P_1O_{41}$$

The solid was passed through a sieve to yield catalyst particles of 35–100 mesh.

An empty U-shaped reactor having inner diameter of 8 mm was filled with 4 ml. of the catalyst. The reactor was placed into a molten salt bath heated at 320°C. A gaseous reactant mixture composed of 55% nitrogen, 30% steam, 10% oxygen and 5% methacrolein (percent by volume) was passed through the reactor with a contact time of 2 seconds. The following results were obtained.

| | |
|---|---|
| Conversion of methacrolein | 83% |
| Selectivity to methacrylic acid | 66% |
| Selectivity to acetic acid | 13% |

EXAMPLES 91 – 99

Catalysts were prepared in a manner similar to that of Example 90, except that 5.0 g of tantalum pentoxide, 1.9 of nickel oxide or 3.8 g of stannous oxide or a combination thereof were used instead of niobium pentoxide so as to give the atomic ratios shown in Table 9. The reaction of Example 90 was repeated using the catalysts. The results obtained are shown in Table 9.

TABLE 9

| Example No. | Catalysts | Methacrolein conversion (%) | Methacrylic acid selectivity (%) | Acetic acid selectivity (%) |
|---|---|---|---|---|
| 91 | $Sb_1Mo_{12}Ta_1P_1O_{41}$ | 67 | 57 | 4 |
| 92 | $Sb_1Mo_{12}Sn_1P_1O_{40.5}$ | 90 | 74 | 11 |
| 93 | $Sb_1Mo_{12}Ni_1P_1O_{39.5}$ | 81 | 69 | 10 |
| 94 | $Sb_1Mo_{12}Nb_1Ta_1P_1O_{43.5}$ | 97 | 54 | 23 |

TABLE 9-continued

| Example No. | Catalysts | Methacrolein conversion (%) | Methacrylic acid selectivity (%) | Acetic acid selectivity (%) |
|---|---|---|---|---|
| 95 | $Sb_1Mo_{12}Nb_1Sn_1P_1O_{43}$ | 91 | 57 | 11 |
| 96 | $Sb_1Mo_{12}Nb_1Ni_1P_1O_{43}$ | 94 | 58 | 7 |
| 97 | $Sb_1Mo_{12}Sn_1Ta_1P_1O_{43}$ | 88 | 60 | 9 |
| 98 | $Sb_1Mo_{12}Sn_1Ni_1P_1O_{41.5}$ | 88 | 64 | 10 |
| 99 | $Sb_1Mo_{12}Ni_1Ta_1P_1O_{42}$ | 85 | 62 | 8 |

REFERENCE C

Catalysts were prepared in a manner similar to that of Examples 90–99 so as to give the atomic ratios shown in Table 10. The reaction of Example 1 was repeated using the catalysts. The results obtained are shown in Table 10.

TABLE 10

| Reference No. | Catalysts | Methacrolein conversion (%) | Methacrylic aicd selectivity (%) | Acetic acid selectivity (%) |
|---|---|---|---|---|
| 12 | $Sb_1Mo_{12}P_1O_{38.5}$ | 90 | 23 | 26 |
| 13 | $Sb_1Ta_1P_1O_{6.5}$ | 41 | 25 | 11 |
| 14 | $Mo_{12}Cr_1P_1O_{40}$ | 64 | 28 | 13 |
| 15 | $Sb_1Mo_{12}Ni_1O_{38.5}$ | 58 | 32 | 8 |
| 16 | $Sb_1Mo_{12}Nb_1Ta_1O_{42.5}$ | 48 | 35 | 7 |
| 17 | $Mo_{12}Nb_1Ta_1P_1O_{43.5}$ | 62 | 37 | 9 |
| 18 | $Mo_{12}Nb_1Sn_1P_1O_{43}$ | 59 | 41 | 8 |
| 19 | $Sb_1Mo_{12}Nb_1Sn_1O_{42}$ | 24 | 25 | 3 |
| 20 | $Sb_1Mo_{12}Nb_1Ni_1O_{41}$ | 28 | 23 | 4 |
| 21 | $Sb_1Mo_{12}Sn_1Ta_1O_{42}$ | 33 | 19 | 3 |
| 22 | $Mo_{12}Sn_1Ta_1P_1O_{42}$ | 61 | 35 | 6 |
| 23 | $Sb_1 Mo_{12}Sn_1Ni_1O_{40.5}$ | 22 | 18 | 2 |
| 24 | $Mo_{12}Sn_1Ni_1P_1O_{41.5}$ | 65 | 39 | 1 |
| 25 | $Sb_1Mo_{12}Ni_1Ta_1O_{41}$ | 48 | 36 | 6 |

EXAMPLE 100

A solution of 5.7 g of antimony trichloride dissolved in 100 cc of 6N-HCl was added with stirring to a solution of 58 g of phosphomolybdic acid ($P_2O_5 \cdot 24MoO_3 \cdot 48H_2O$) dissolved in 150 cc of water. To the resulting solution was added 3.3 g of niobium pentoxide followed by 2.0 g of iron oxide. The mixture was heated with stirring to concentrate it. The resultant cake was dried at 120°C for 12 hours and the dried product was calcined at 400°C for 12 hours to yield a solid having the following empirical formula $Sb_1Mo_{12}Nb_1Fe_1P_1O_{42.5}$ The solid was passed through a sieve to yield catalyst particles 35–100 mesh.

An empty U-shaped reactor having inner diameter of 8 mm was filled with 4 ml. of the catalyst. The reaction of Example 90 was repeated using the catalysts. The following results were obtained.

| | |
|---|---|
| Conversion of methacrolein | 95% |
| Selectivity to methacrylic acid | 58% |
| Selectivity to acetic acid | 12% |

EXAMPLES 101–109

Catalysts were prepared in a manner similar to that of Example 100, except that 1.9 g of nickel oxide, 3.8 g of stannous oxide or 5.0 g of tantalum oxide were used instead of niobium pentoxide, and 3.1 g of strontium oxide or 2.0 g of titanium oxide was used instead of iron oxide so as to give the emperical formula shown in Table 11. The reaction of Example 90 was repeated using the catalysts. The following results were obtained.

TABLE 11

| Example No. | Catalysts | Methacrolein conversion (%) | Methacrylic acid selectivity (%) | Acetic acid selectivity (%) |
|---|---|---|---|---|
| 101 | $Sb_1Mo_{12}Nb_1Fe_1P_1O_{42.5}$ | 73 | 73 | 8 |
| 102 | $Sb_1Mo_{12}Ni_1Fe_1P_1O_{41}$ | 92 | 61 | 11 |
| 103 | $Sb_1Mo_{12}Sn_1Fe_1P_1O_{42}$ | 82 | 70 | 8 |
| 104 | $Sb_1Mo_{12}Ta_1Fe_1P_1O_{41.5}$ | 73 | 60 | 10 |
| 105 | $Sb_1Mo_{12}Ni_1Sr_1P_1O_{40.5}$ | 84 | 63 | 8 |
| 106 | $Sb_1Mo_{12}Sn_1Sr_1P_1O_{41.5}$ | 88 | 71 | 11 |
| 107 | $Sb_1Mo_{12}Sn_1Zr_1P_1O_{42.5}$ | 83 | 60 | 11 |
| 108 | $Sb_1Mo_{12}Ni_1Zr_1P_1O_{41.5}$ | 82 | 58 | 12 |

TABLE 11-continued

| Example No. | Catalysts | Methacrolein conversion (%) | Methacrylic acid selectivity (%) | Acetic acid selectivity (%) |
|---|---|---|---|---|
| 109 | $Sb_1Mo_{12}Ta_1Ti_1P_1O_{43}$ | 96 | 58 | 16 |

EXAMPLES 110–123

The catalysts prepared by the procedure of Examples 90–109 were used for the oxidation of acrolein instead of methacrolein under substantially the same conditions as those employed in Example 90, except that the reaction temperature was 360°C. The results are shown in Table 12.

TABLE 12

| Example No. | Catalysts | Acrolein conversion (%) | Acrylic acid selectivity (%) | Acetic acid selectivity (%) |
|---|---|---|---|---|
| 110 | $Sb_1Mo_{12}Nb_1P_1O_{41}$ | 95 | 76 | 15 |
| 111 | $Sb_1Mo_{12}Sn_1P_1O_{40.5}$ | 91 | 72 | 12 |
| 112 | $Sb_1Mo_{12}Ni_1P_1O_{39.5}$ | 97 | 71 | 16 |
| 113 | $Sb_1Mo_{12}Nb_1Ta_1P_1O_{43.5}$ | 97 | 67 | 15 |
| 114 | $Sb_1Mo_{12}Nb_1Sn_1P_1O_{43}$ | 93 | 65 | 14 |
| 115 | $Sb_1Mo_{12}Nb_1Ni_1P_1O_{42}$ | 94 | 63 | 7 |
| 116 | $Sb_1Mo_{12}Sn_1Ta_1P_1O_{43}$ | 87 | 69 | 9 |
| 117 | $Sb_1Mo_{12}Ni_1Ta_1P_1O_{42}$ | 88 | 67 | 10 |
| 118 | $Sb_1Mo_{12}Nb_1Fe_1P_1O_{42.5}$ | 96 | 65 | 15 |
| 119 | $Sb_1Mo_{12}Nb_1Mg_1P_1O_{42}$ | 88 | 75 | 9 |
| 120 | $Sb_1Mo_{12}Ni_1Fe_1P_1O_{41}$ | 94 | 67 | 13 |
| 121 | $Sb_1Mo_{12}Sn_1Sr_1P_1O_{41.5}$ | 90 | 65 | 13 |
| 122 | $Sb_1Mo_{12}Ni_1Zr_1P_1O_{41.5}$ | 92 | 64 | 13 |
| 123 | $Sb_1Mo_{12}Ta_1Ti_1P_1O_{43}$ | 97 | 63 | 17 |

EXAMPLES 133 – 142

Catalysts were prepared in a manner similar to that of Example 90 so as to give the atomic ratios shown in Table 13. The reaction of Example 90 was repeated using the catalyst at 320°C and feeding in methacrolein. The results obtained are shown in Table 13.

TABLE 13

| Example No. | Catalysts | Methacrolein conversion (%) | Methacrylic acid selectivity (%) | Acetic acid selectivity (%) |
|---|---|---|---|---|
| 124 | $Sb_3Mo_{12}Nb_1P_1O_{41}$ | 88 | 60 | 8 |
| 125 | $Sb_3Mo_{12}Nb_3P_1O_{46}$ | 81 | 62 | 11 |
| 126 | $Sb_5Mo_{12}Sn_1P_5O_{50.5}$ | 54 | 51 | 7 |
| 127 | $Sb_1Mo_{12}Sn_1P_5O_{50.5}$ | 21 | 75 | 2 |
| 128 | $Sb_1Mo_{12}Ni_6Fe_1P_1O_{46}$ | 85 | 53 | 4 |
| 129 | $Sb_1Mo_{12}Ta_1Fe_6P_1O_{50}$ | 71 | 54 | 12 |
| 130 | $Sb_3Mo_{12}Ni_1Sr_1P_1O_{40.5}$ | 82 | 65 | 10 |
| 131 | $Sb_1Mo_{12}Sn_3Sr_1P_1O_{45.5}$ | 85 | 66 | 15 |
| 132 | $Sb_1Mo_{12}Sn_3Sr_1P_2O_{48}$ | 75 | 67 | 13 |
| 133 | $Sb_1Mo_{12}Ni_3Zr_1P_1O_{43.5}$ | 80 | 61 | 9 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for preparing methacrylic acid, which comprises:
reacting methacrolein with molecular oxygen in the vapor phase at a temperature of from 250° to 450°C, in the presence of a catalyst consisting essentially of (a) molybdenum, (b) phosphorous, (c) antimony, (d) at least one element, but not more than any two elements selected from the group consisting of tungsten, barium, chromium, lead, niobium, tantalum, tin, nickel, iron and zirconium, and (e) oxygen.

2. The process of claim 1, wherein said catalyst has the empirical formula:

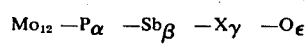

$$Mo_{12}-P_\alpha-Sb_\beta-X_\gamma-O_\epsilon$$

wherein X is at least one element selected from the group consisting of tungsten, barium, chromium, lead, niobium, tantalum, tin, nickel, iron and zirconium; $\alpha$ is a number from 0.1 to 3; $\beta$ is a number from 0.1 to 9; $\gamma$ is a number from 0.1 to 7; $\delta$ is decided on the basis of the oxidation states of the other elements.

3. A process for preparing methacrylic acid, which comprises:
reacting methacrolein with molecular oxygen in the vapor phase at a temperature of from 250° to 450°C, in the presence of a catalyst consisting essentially of (a) molybdenum, (b) phosphorous, (c) antimony, (d) at least one element, but not more than any two elements selected from the group consisting of tungsten, barium, chromium, lead, niobium, tantalum, tin, nickel, iron and zirconium, (e) oxygen, and (f) at least one element selected from the group consisting of strontium, titanium, germanium, cerium and silver.

4. The process of claim 3, wherein said catalyst has the empirical formula:

$$Mo_{12} - P_\alpha - Sb_\beta - X_\gamma - Y_\epsilon - O_\delta$$

wherein X is at least one element selected from the group consisting of tungsten, barium, chromium, lead, niobium, tantalum, tin, nickel, iron and zirconium; Y is at least one element selected from the group consisting of strontium, titanium, germanium, cerium, and silver; $\alpha$ is a number from 0.1 to 3; $\beta$ is a number from 0.1 to 9; $\gamma$ is a number from 0.1 to 7; $\epsilon$ is a number from 0.1 to 7; $\delta$ is decided on the basis of the oxidation states of the other elements.

5. A process for preparing methacrylic acid, which comprises:
reacting methacrolein with molecular oxygen in the vapor phase at a temperature of from 250° to 450°C, in the presence of a catalyst which has the empirical formula consisting essentially of:

$$Mo_{12} - P_\alpha - Sb_\beta - X_\gamma - O_\delta$$

wherein X is at least one element selected from the group consisting of tungsten, barium, chromium and lead; $\alpha$ is a number from 0.1 to 3, $\beta$ is a number 0.1 to 9; $\gamma$ is a number from 0.1 to 7; $\delta$ is decided on the basis of the oxidation states of the other elements.

6. A process for preparing methacrylic acid, which comprises:
reacting methacrolein with molecular oxygen in the vapor phase at a temperature of from 250° to 450°C, in the presence of a catalyst which has the empirical formula consisting essentially of:

$$Mo_{12} - P_\alpha - Sb_\beta - X_\gamma - Y_\epsilon - O_\delta$$

wherein X is at least one element selected from the group consisting of niobium, tantalum, tin and nickel; Y is at least one element selected from the group consisting of zirconium, strontium and titanium; $\alpha$ is a number from 0.1 to 3; $\beta$ is a number from 0.1 to 9; $\gamma$ is a number from 0.1 to 7; $\epsilon$ is a number from 0.1 to 7; $\delta$ is decided on the basis of the oxidation states of the other elements.

7. A process for preparing methacrylic acid, which comprises:
reacting methacrolein with molecular oxygen in the vapor phase at a temperature of from 250° to 450°C, in the presence of a catalyst which has the empirical formula consisting essentially of:

$$Mo_{12} - P_\alpha - Sb_\beta - X_\gamma - Y_\epsilon - O_\delta$$

wherein X is zirconium; Y is one element selected from the group consisting of germanium, cerium, silver and titanium; $\alpha$ is a number from 0.1 to 3; $\beta$ is a number from 0.1 to 9; $\gamma$ is a number from 0.1 to 7; $\epsilon$ is a number from 0.1 to 7; $\delta$ is decided on the basis of the oxidation states of the other elements.

8. The process of claim 1, wherein said catalyst is prepared by concentrating a solution or a suspension containing the desired components, drying the resulting concentrate, calcining the dried product at a temperature from 250°C to 450°C for 1 to 48 hours in air, and grinding said dried product into 35–100 mesh particles.

* * * * *